US008052423B2

(12) United States Patent
Ali Alghamdi

(10) Patent No.: US 8,052,423 B2
(45) Date of Patent: Nov. 8, 2011

(54) TUNNELING METHOD FOR DENTAL BLOCK GRAFTING

(75) Inventor: Ali Saad Ali Alghamdi, Jeddah (SA)

(73) Assignee: King Abdulaziz University, Jeddah (SA)

( * ) Notice: Subject to any disclaimer, the term of this patent is extended or adjusted under 35 U.S.C. 154(b) by 271 days.

(21) Appl. No.: 12/461,757

(22) Filed: Aug. 24, 2009

(65) Prior Publication Data

US 2011/0045438 A1    Feb. 24, 2011

(51) Int. Cl.
*A61C 5/00* (2006.01)
*A61C 13/12* (2006.01)
*A61C 13/225* (2006.01)
*A61C 8/00* (2006.01)

(52) U.S. Cl. ...................................................... 433/215
(58) Field of Classification Search .......... 433/172–176, 433/215; 606/80, 92, 190, 214, 191–192, 606/60, 246, 279, 300, 86 R, 331, 76; 623/11.11
See application file for complete search history.

(56) References Cited

U.S. PATENT DOCUMENTS

| | | | | |
|---|---|---|---|---|
| 4,755,184 A | * | 7/1988 | Silverberg | 623/23.56 |
| 4,787,906 A | * | 11/1988 | Haris | 623/23.72 |
| 4,863,472 A | * | 9/1989 | Tormala et al. | 623/23.58 |
| 4,997,433 A | | 3/1991 | Goble et al. | |
| 5,139,520 A | * | 8/1992 | Rosenberg | 606/87 |
| 5,306,240 A | | 4/1994 | Berry | |
| 7,033,364 B1 | | 4/2006 | Walters et al. | |
| 7,144,413 B2 | | 12/2006 | Wilford et al. | |
| 7,279,008 B2 | | 10/2007 | Brown et al. | |
| 7,341,592 B1 | | 3/2008 | Walters et al. | |
| 7,396,232 B2 | | 7/2008 | Fromovich et al. | |
| 2002/0009692 A1 | | 1/2002 | Ashman | |
| 2003/0105469 A1 | * | 6/2003 | Karmon | 606/92 |
| 2005/0142518 A1 | * | 6/2005 | Gross | 433/215 |
| 2006/0173467 A1 | | 8/2006 | Karwoski et al. | |
| 2008/0058928 A1 | * | 3/2008 | Raphael et al. | 623/11.11 |
| 2009/0054928 A1 | | 2/2009 | Denham et al. | |

FOREIGN PATENT DOCUMENTS

WO    WO02060333 (A1)    8/2002

OTHER PUBLICATIONS

A.S.T. AlGhamdi and R.J. Buhite, "A New Tunnel Technique With Acellular Dermal Matrix For Soft Tissue Preparation Prior to Symphyseal Block Graft—A Description of Technique and Case Report", *Journal of Oral Implantology*, vol. XXXIV, No. 5, 274-280, Oct. 2008.

* cited by examiner

*Primary Examiner* — Todd Manahan
*Assistant Examiner* — Yogesh Patel
(74) *Attorney, Agent, or Firm* — Richard C. Litman

(57) ABSTRACT

The tunneling method for dental block grafting is surgical method for increasing the thickness of the soft tissue of the mouth prior to performing block grafting procedures for dental implants. The method includes cutting a pair of incisions in the mucosa. A tunnel is formed through the mucosa which extends between, and connects, the pair of incisions. The tunnel is then extended coronally to undermine tissue covering the recipient site. An acellular dermal matrix is then sutured to an exposed end of a dental implement pulled through the tunnel to position the acellular dermal matrix within the tunnel. The acellular dermal matrix is then positioned over the recipient site using a periosteal elevator, and the acellular dermal matrix is fixed coronally by suspension sutures. The pair of incisions are closed with interrupted sutures, and a block graft is fixed to the recipient site by a pair of titanium screws.

14 Claims, 14 Drawing Sheets

TUNNELING METHOD FOR DENTAL BLOCK GRAFTING

BACKGROUND OF THE INVENTION

1. Field of the Invention

The present invention relates to oral surgery methods, and particularly to a tunneling method for dental block grafting that increases the thickness of the soft tissue of the mouth prior to performing block grafting procedures for dental implants.

2. Description of the Related Art

A dental implant is an artificial tooth root replacement and is used in prosthetic dentistry to support restorations that resemble a tooth or group of teeth. Prior to commencement of surgery, careful and detailed planning is required to indentify vital structures such as the inferior alveolar nerve or the sinus and to properly orientate the implants for the most predictable outcome. Two-dimensional radiographs, such as periapicals or orthopantomographs, are taken prior to the surgery.

In its most basic form, the placement of an osseointegrated implant requires a preparation into the bone using either hand osteotomes or precision drills with highly regulated speed to prevent burning or pressure necrosis of the bone. After a variable amount of time to allow the bone to grow onto the surface of the implant (osseointegration), a tooth or teeth can be placed on the implant. The amount of time required to place an implant will vary depending on the experience of the practitioner and difficulty of the individual situation.

At edentulous (without teeth) jaw sites, a pilot hole is bored into the recipient bone, taking care to avoid the vital structures (in particular the inferior alveolar nerve (IAN) and the mental foramen within the mandible). Drilling into jawbone usually occurs in several separate steps. The pilot hole is expanded by using progressively wider drills (typically between three and seven successive drilling steps, depending on implant width and length). Care is taken not to damage the osteoblast or bone cells by overheating. The implant screw can be self-tapping, and is screwed into place at a precise torque so as not to overload the surrounding bone (overloaded bone can die, a condition called osteonecrosis, which may lead to failure of the implant to fully integrate or bond with the jawbone). Typically, in most implant systems, the osteotomy or drilled hole is about 1 mm deeper than the implant being placed, due to the shape of the drill tip. Surgeons must take the added length into consideration when drilling in the vicinity of vital structures.

Traditionally, an incision is made over the crest of the site where the implant is to be placed. This is referred to as a "flap". Some systems allow for "flapless" surgery, where a piece of mucosa is punched-out from over the implant site. Proponents of "flapless" surgery believe that it decreases recovery time, while its detractors believe it increases complication rates because the edge of bone cannot be visualized. Because of these visualization problems, flapless surgery is often carried out using a surgical guide constructed following computerized 3D-planning of a pre-operative CT scan. The amount of time required for an implant to become osseointegrated is a widely debated topic. Consequently, the amount of time that practitioners allow the implant to heal before placing a restoration on it varies widely. In general, practitioners allow 2 to 6 months for healing, but preliminary studies show that early loading of implant may not increase early or long term complications.

When an implant is placed, either a healing abutment, which comes through the mucosa, is placed, or a "cover screw" is used, which is flush with the surface of the dental implant. When a cover screw is placed, the mucosa covers the implant while it integrates, then a second surgery is completed to place the healing abutment. Two-stage surgery is sometimes chosen when a concurrent bone graft is placed or surgery on the mucosa may be required for esthetic reasons. Some implants are one piece so that no healing abutment is required.

For a dental implant procedure to work, there must be enough bone in the jaw, and the bone has to be strong enough to hold and support the implant. If there is not enough bone, more may need to be added with a bone graft procedure. In cases with severe ridge deficiency, block grafting is the recommended procedure to build the ridge prior to dental implant placement. One of the most important factors in the success of block grafts is adequate and maintained soft tissue coverage. Mucosal dehiscence and premature exposure of the autogenous block graft are the most common cause of graft failure.

Thus, a tunneling method for dental block grafting solving the aforementioned problems is desired.

SUMMARY OF THE INVENTION

The tunneling method for dental block grafting is a surgical method for increasing the thickness of the soft tissue of the mouth prior to performing block grafting procedures for dental implants. The tunneling method is useful for patients with relatively thin soft tissue or mucosa. By increasing the thickness of the soft tissue, common soft tissue complications around the block grafts are minimized. The method begins with the cutting of a pair of incisions in the mucosa of the patient's mouth. Each incision is cut approximately equidistant from a recipient site for the dental implant (i.e., about the alveolus of a missing tooth or other dental defect). Each incision is preferably formed a distance of at least one-and-a-half tooth widths from the recipient site and extends apically from just above the mucogingival junction. Each incision is formed with a length between approximately 5 and 7 mm.

A tunnel is formed through the mucosa which extends between, and connects, the pair of incisions. The tunnel is formed by partial-thickness dissection of the mucosa using a dental implement, such as a periosteal elevator, with the dental implement extending through the tunnel. The tunnel is then extended coronally to undermine tissue covering the recipient site.

An acellular dermal matrix is then sutured to an exposed end of the dental implement, preferably by a single knot formed on the exposed end, and the dental implement is pulled through the tunnel to position the acellular dermal matrix within the tunnel. The acellular dermal matrix is then positioned over the recipient site using a periosteal elevator, and the acellular dermal matrix is fixed coronally by five suspension sutures.

The pair of incisions are then closed with interrupted sutures. Preferably, the patient is allowed a healing time of approximately eight weeks, then the block graft is fixed to the recipient site by pair of titanium screws. Deficiencies at the edges of the graft may be then filled with particulate bone graft.

These and other features of the present invention will become readily apparent upon further review of the following specification and drawings.

DETAILED DESCRIPTION OF THE PREFERRED EMBODIMENTS

Figure 2:
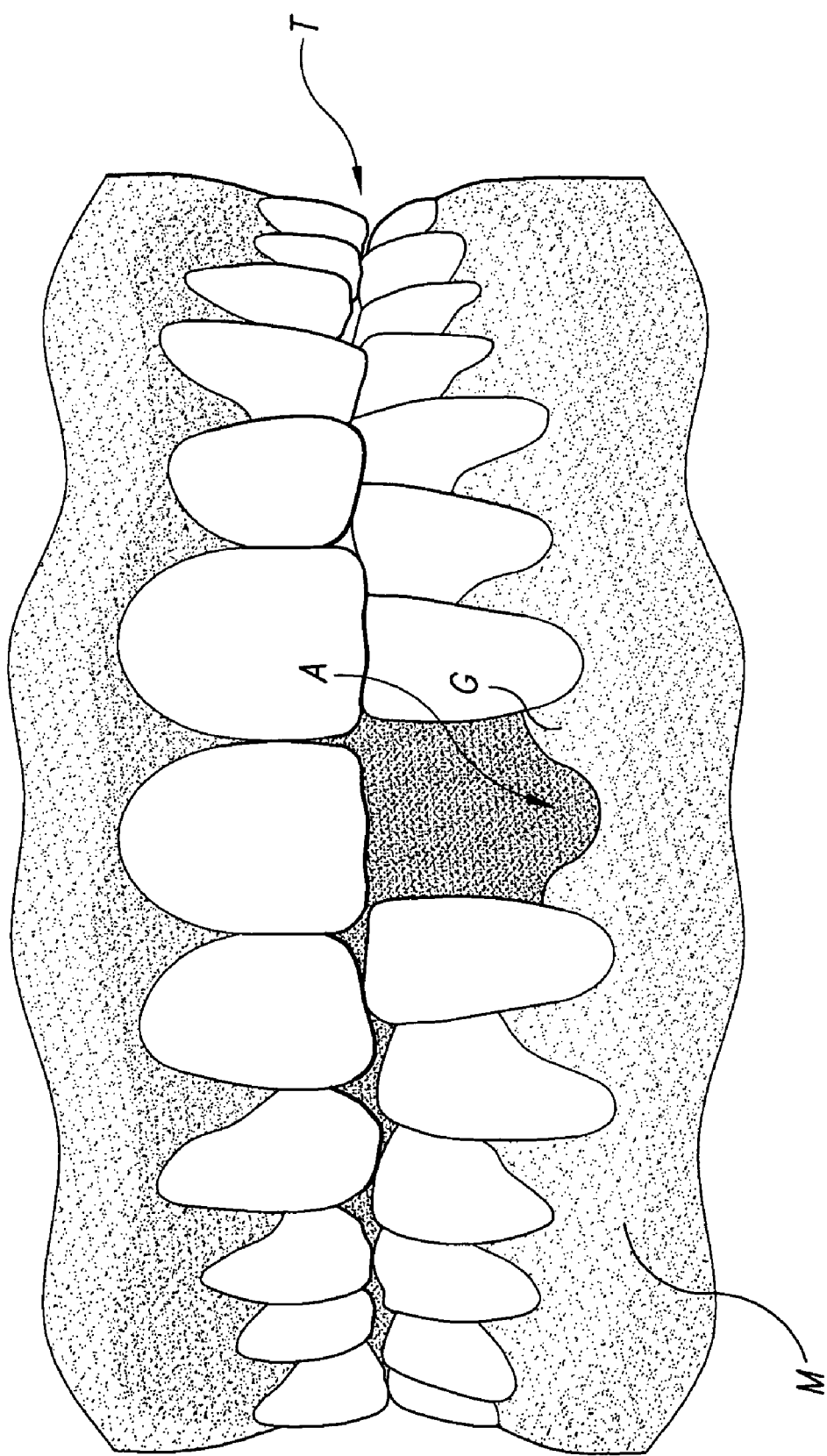
FIG. 2 is a partial front view showing a set of teeth having a missing central incisor with a class III ridge defect and thin mucosa.

FIG. 2 illustrates the teeth T of a patient missing a mandibular central incisor (leaving an exposed alveolus) with a class III ridge defect a relatively thin mucosa M. The present tunneling method for dental block grafting is a surgical method for increasing the thickness of the soft tissue of the mouth prior to performing block grafting procedures for dental implants, such as that needed by the patient shown in FIG. 2, for example. The tunneling method is particularly utilized for patients with relatively thin soft tissue or mucosa M. By increasing the thickness of the soft tissue, common soft tissue complications around the block grafts are minimized.

Figure 3:
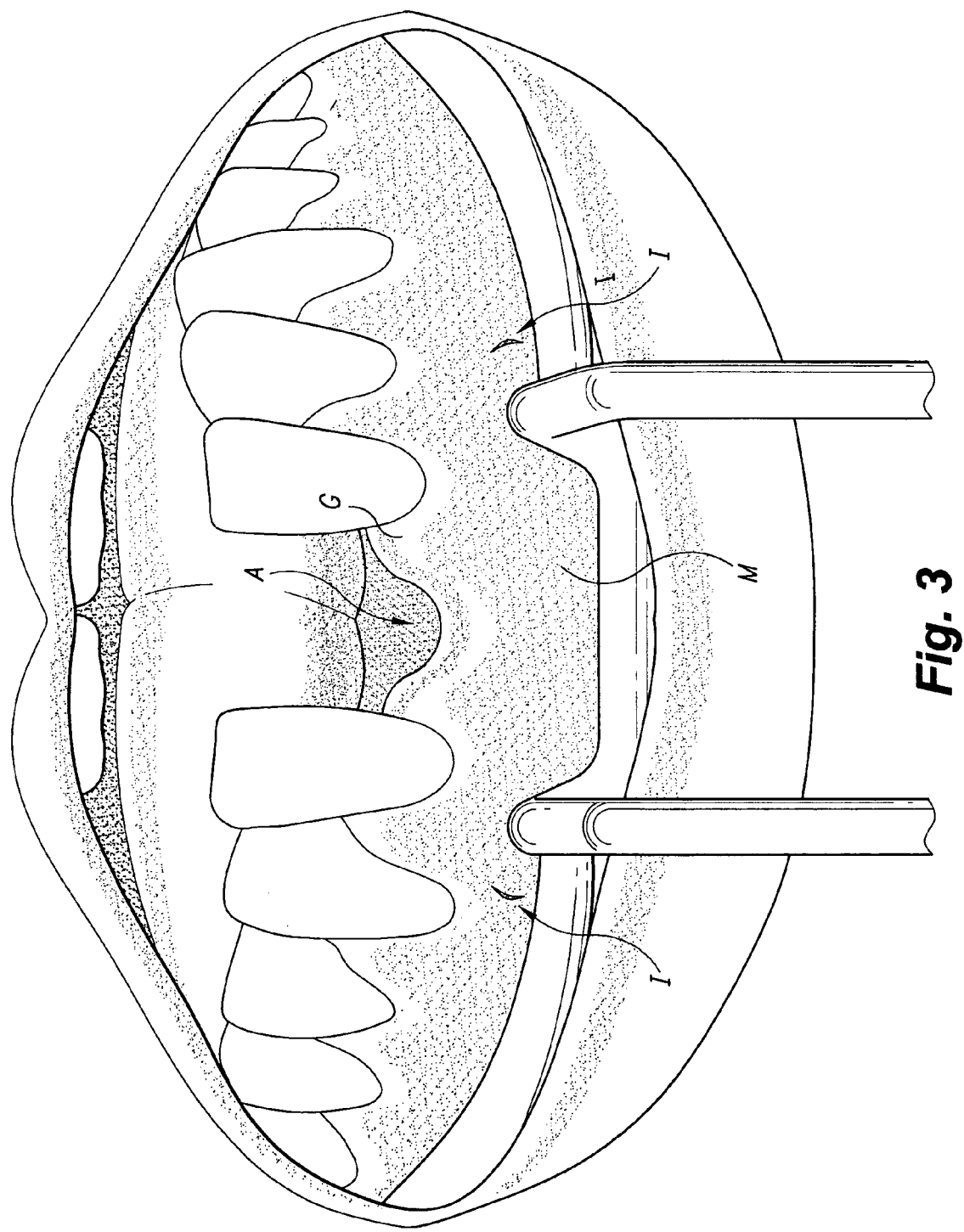
FIG. 3 is a partial front view showing the step of forming a pair of vertical incisions in the patient's mucosa in the tunneling method for dental block grafting according to the present invention.

The recipient site is first anesthetized using local infiltration with, for example, 2% lidocaine, containing 1:100,000 epinephrine. As shown in FIG. 3, the method begins with the cutting of a pair of incisions I in the mucosa M of the patient's mouth (step 10 in FIG. 1). Each incision I is cut approximately equidistant from the recipient site for the dental implant (i.e., about the alveolus A of the missing tooth or other dental defect). Each incision I is preferably formed a distance of at least one-and-a-half tooth widths mesiodistally from the recipient site and extends apically from just above the mucogingival junction J (i.e., the junction between the gingival G and the mucosa M). Each incision I is preferably formed with a length between approximately 5 and 7 mm.

Figure 1:
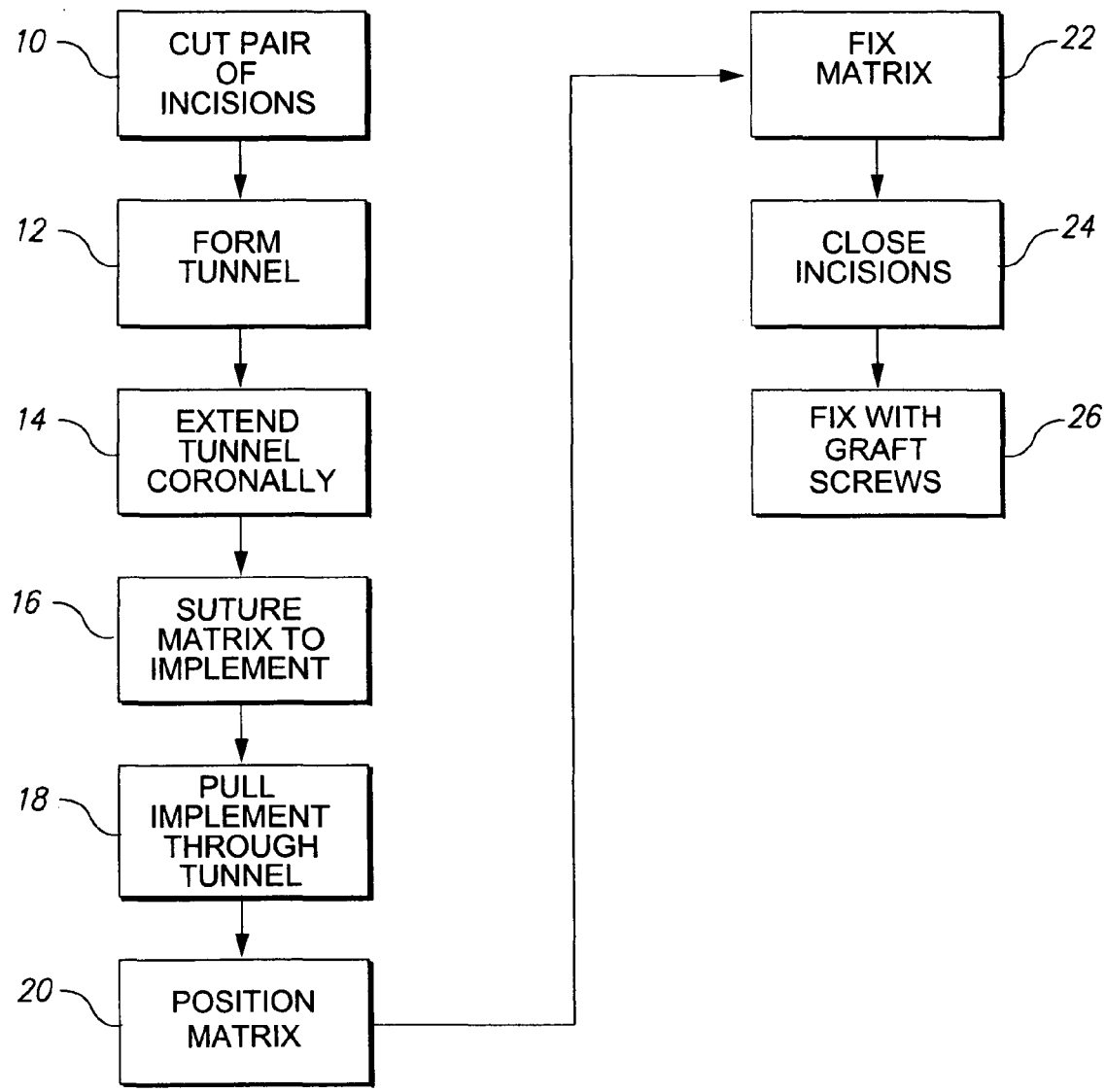
FIG. 1 is a block diagram illustrating the steps of the tunneling method for dental block grafting according to the present invention.
Figure 4:
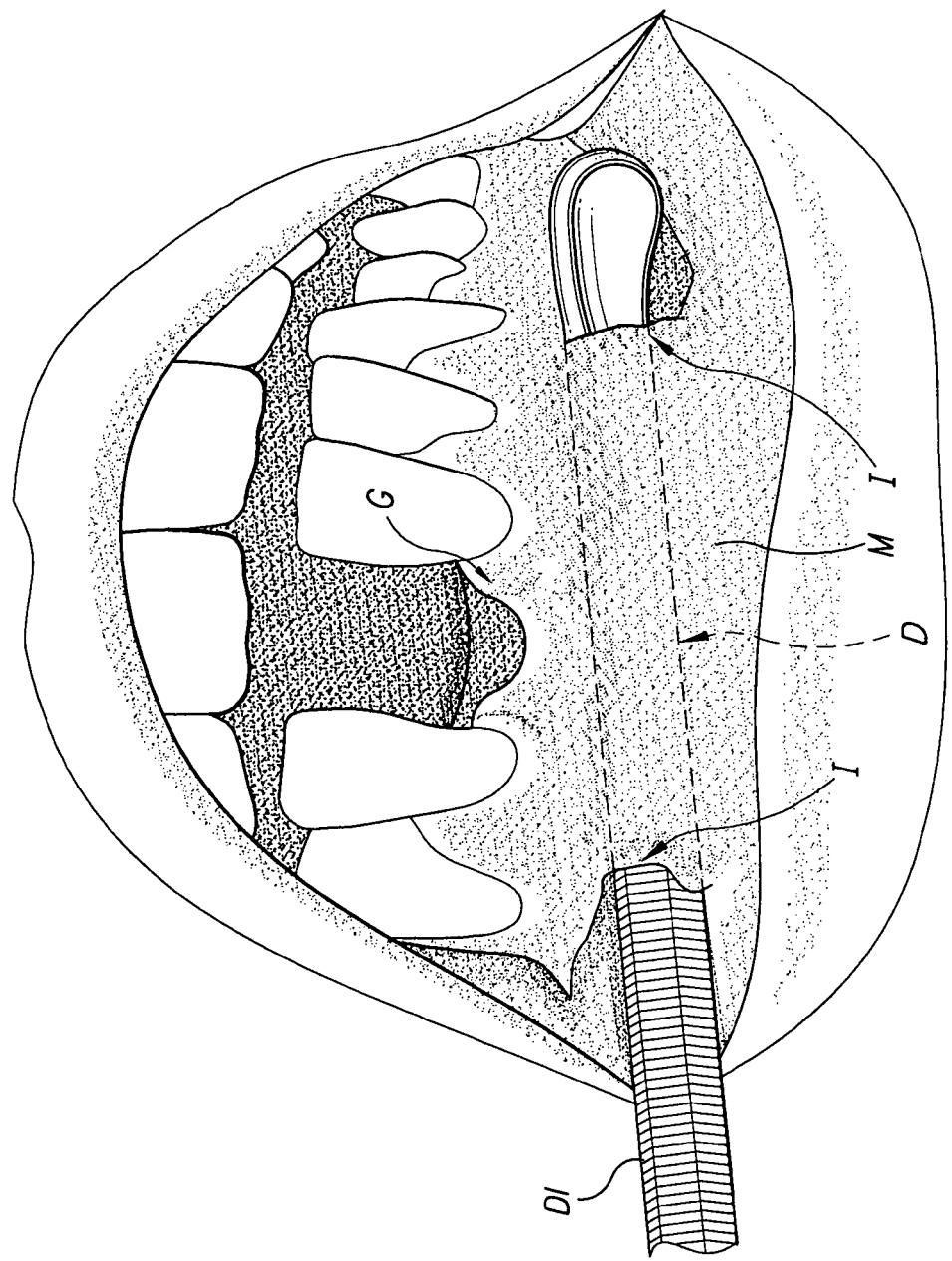
FIG. 4 is a partial front view showing the step of forming a partial thickness dissection between the pair of vertical incisions in the tunneling method for dental block grafting according to the present invention.
Figure 5:
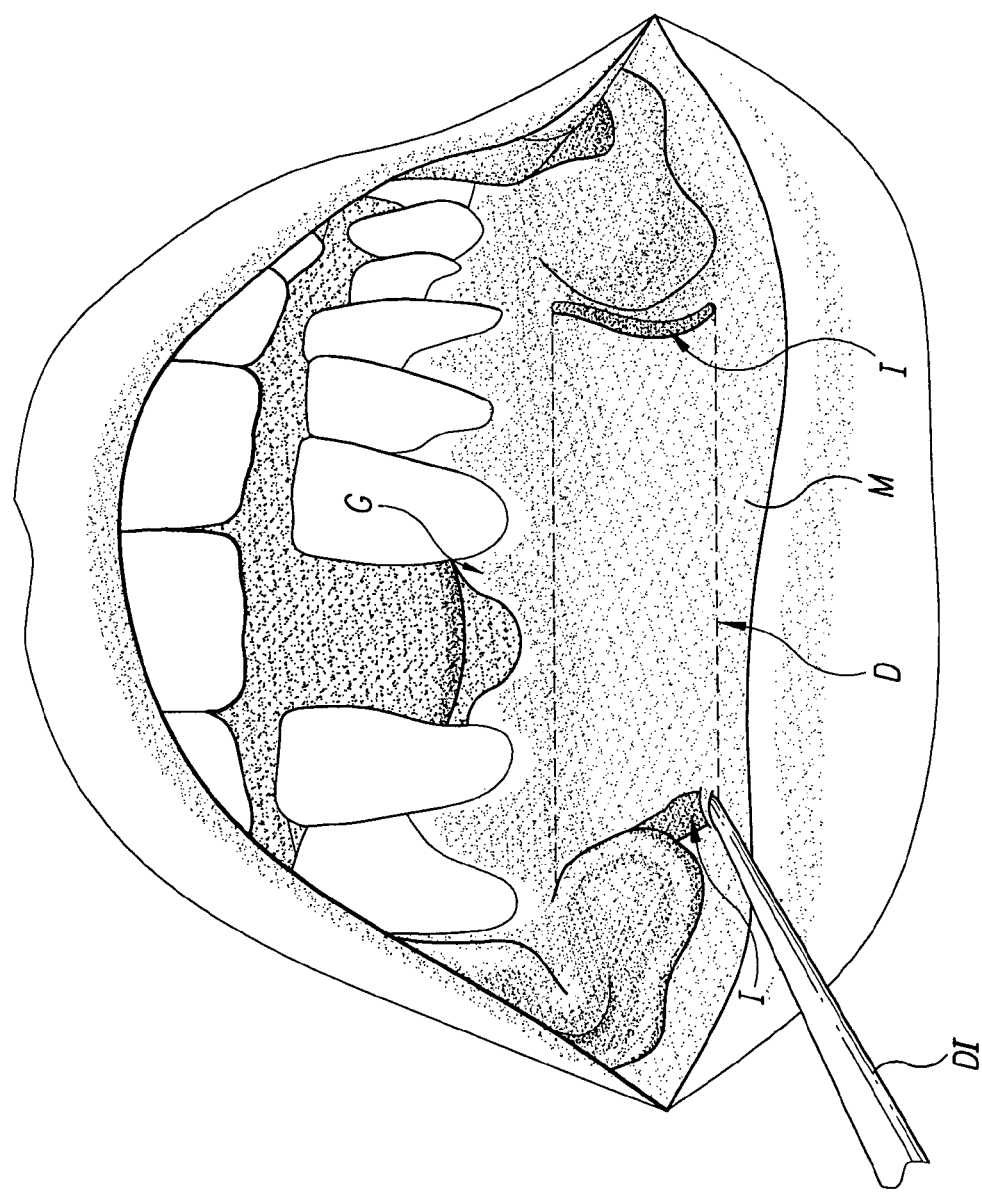
FIG. 5 is a partial front view showing the step of making a coronal extension of the partial-thickness dissection of FIG. 4 in the tunneling method for dental block grafting according to the present invention.

As shown in FIG. 4, a tunnel D is formed through the mucosa M which extends between, and connects, the pair of incisions I. The tunnel D is formed by partial-thickness dissection of the mucosa M using a dental implement DI, such as a periosteal elevator, with the dental implement DI extending through the tunnel D (step 12 of FIG. 1). The tunnel D is then extended coronally to undermine the tissue covering the recipient site (step 14 of FIG. 1, shown in FIG. 5).

Figure 6:
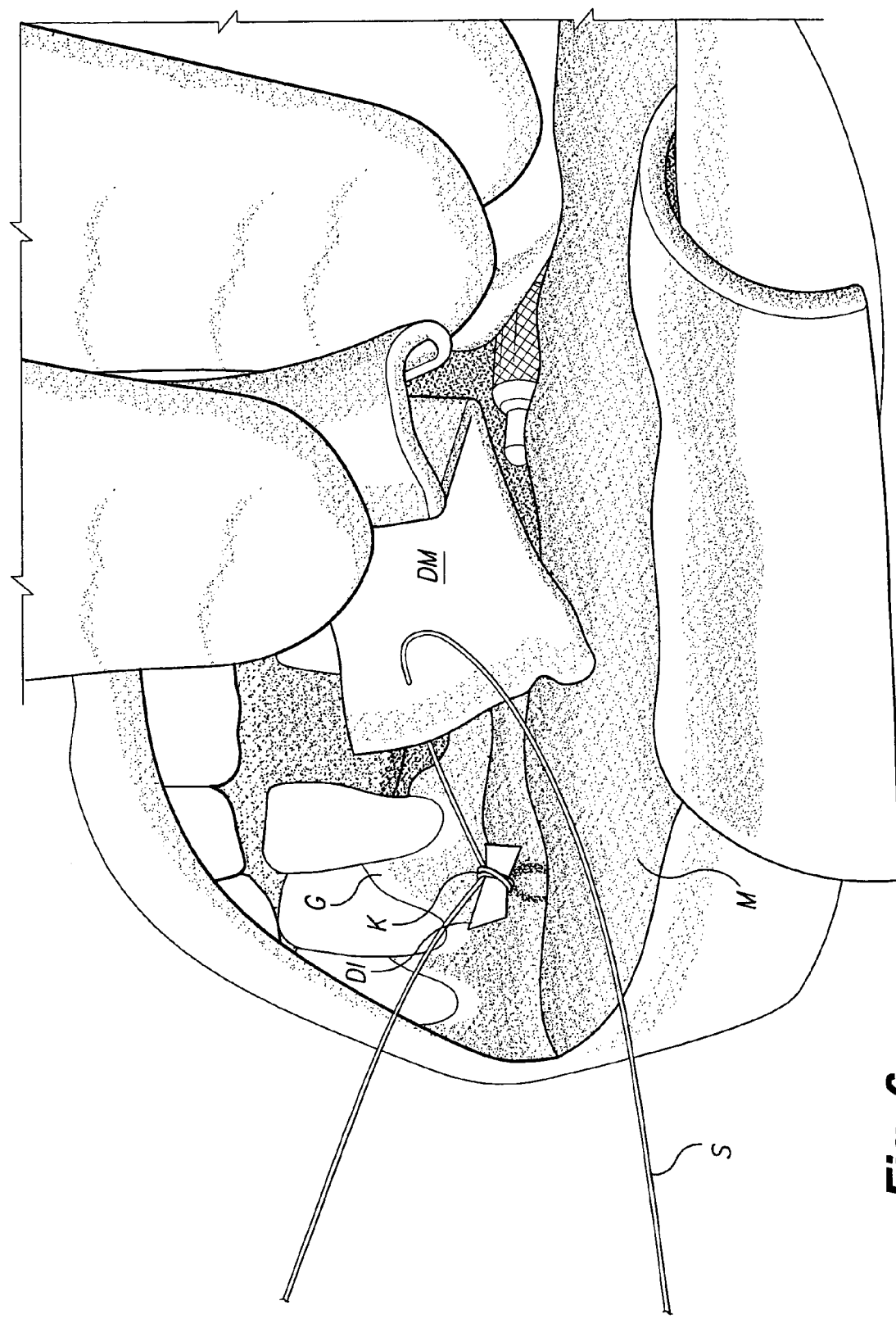
FIG. 6 is a partial front view showing the step of suturing an acellular dermal matrix to a dental implement extending through the partial-thickness dissection of FIG. 5 in the tunneling method for dental block grafting according to the present invention.
Figure 7:
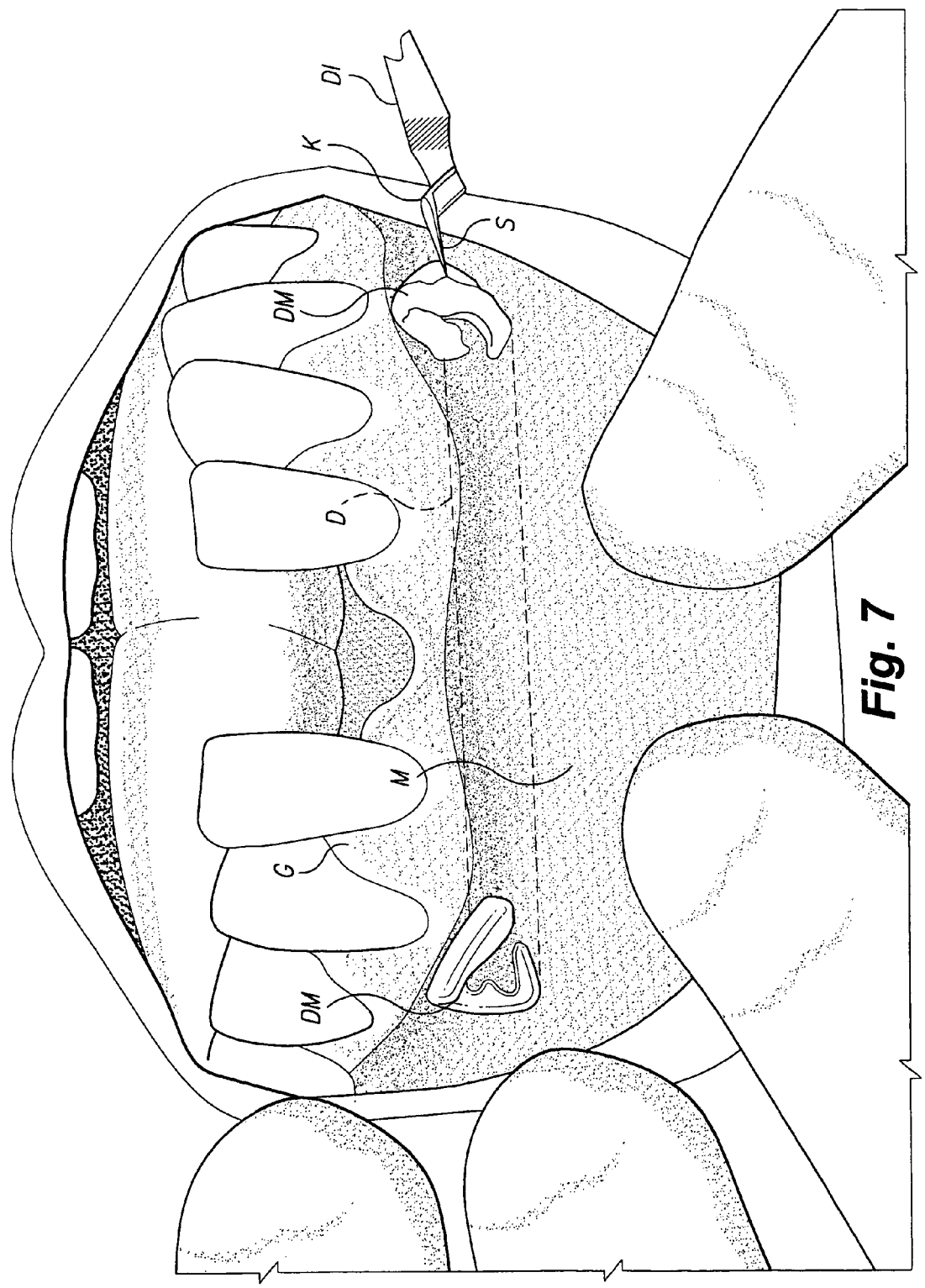
FIG. 7 is a partial front view showing the step of pulling the dental implement through the partial-thickness dissection in the tunneling method for dental block grafting according to the present invention.
Figure 8:
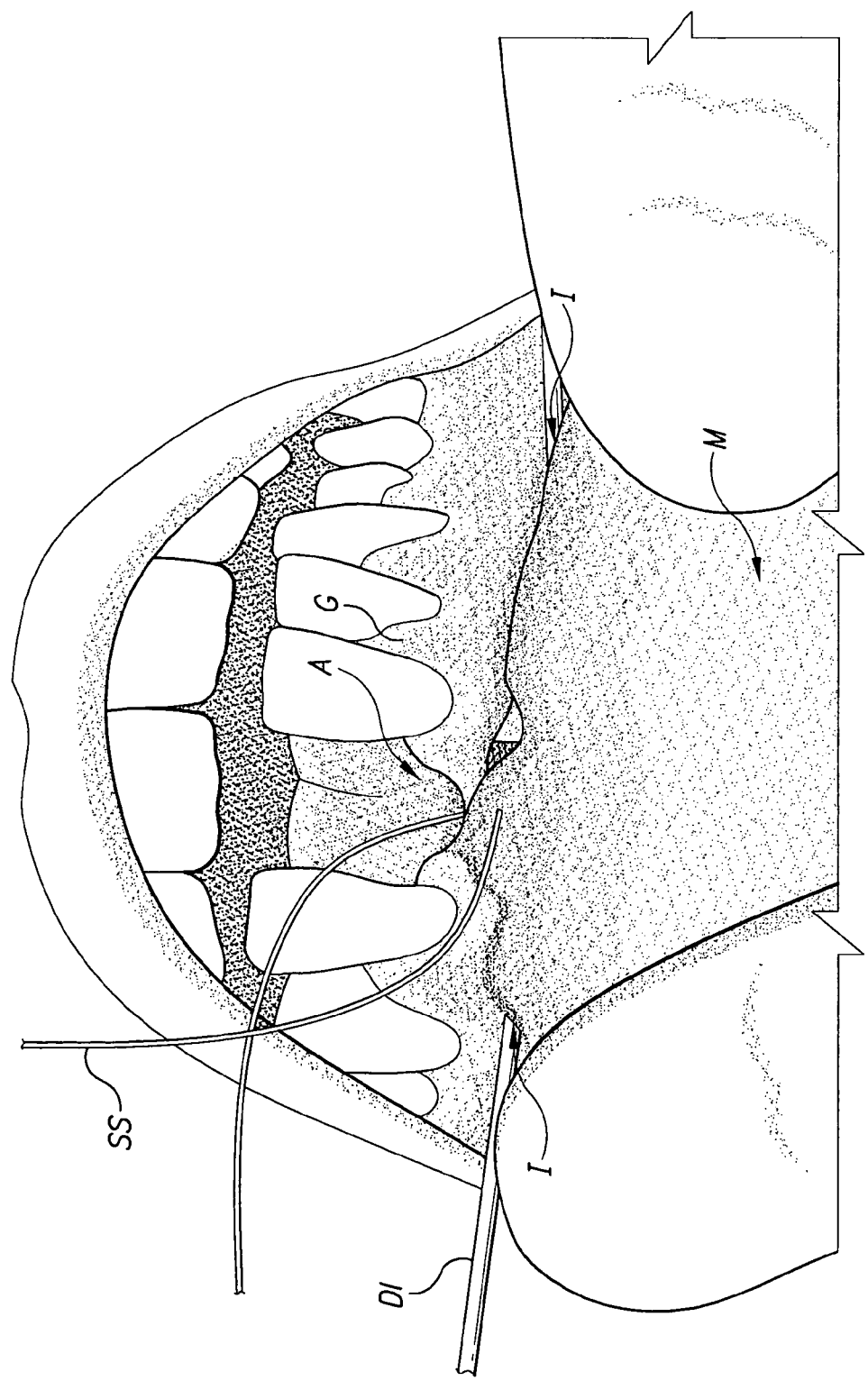
FIG. 8 is a partial perspective view showing the step of positioning and fixing the acellular dermal matrix in the tunneling method for dental block grafting according to the present invention.
Figure 9:
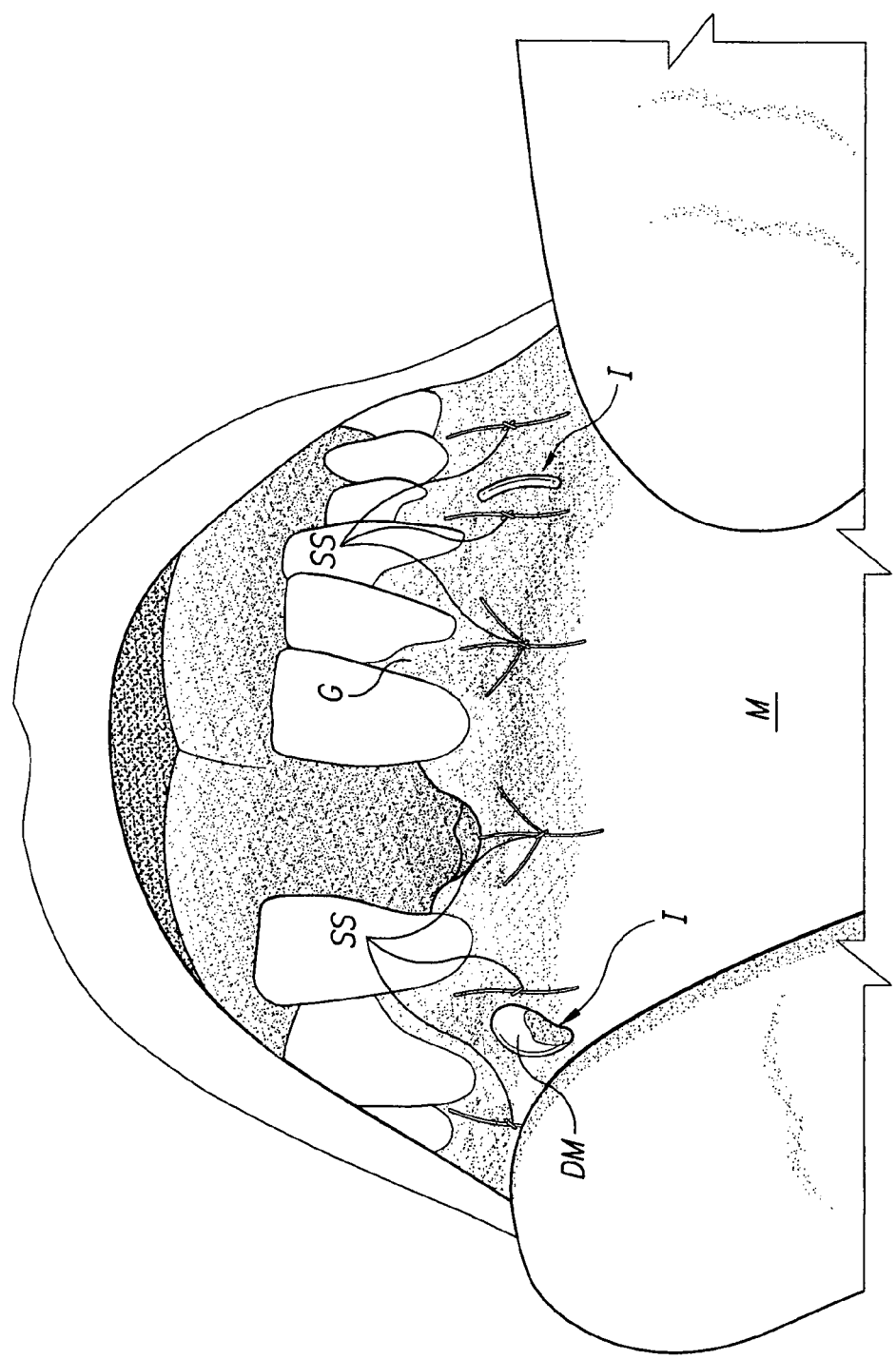
FIG. 9 is a partial perspective view showing the step of suturing the acellular dermal matrix of FIG. 8 in position in the tunneling method for dental block grafting according to the present invention.

An acellular dermal matrix DM is then sutured by suture S to an exposed end of the dental implement DI, preferably by a single knot K formed on the exposed end (step 16, shown in FIG. 6), and the dental implement DI is pulled through the tunnel D to position the acellular dermal matrix DM within the tunnel D (step 18, shown in FIG. 7). Dermal matrix DM is preferably hydrated prior to insertion through tunnel D. Any suitable type of dermal matrix may be utilized. Acellular dermal matrix allografts are well known in the field of dental implantation. One such matrix material is sold under the mark AllDerm® by the LifeCell Corporation of Delaware. As shown in FIG. 8, the acellular dermal matrix DM is then positioned over the recipient site using a periosteal elevator (step 20), and the acellular dermal matrix DM is fixed coronally by five suspension sutures SS (step 22, shown in FIG. 9).

Figure 10:
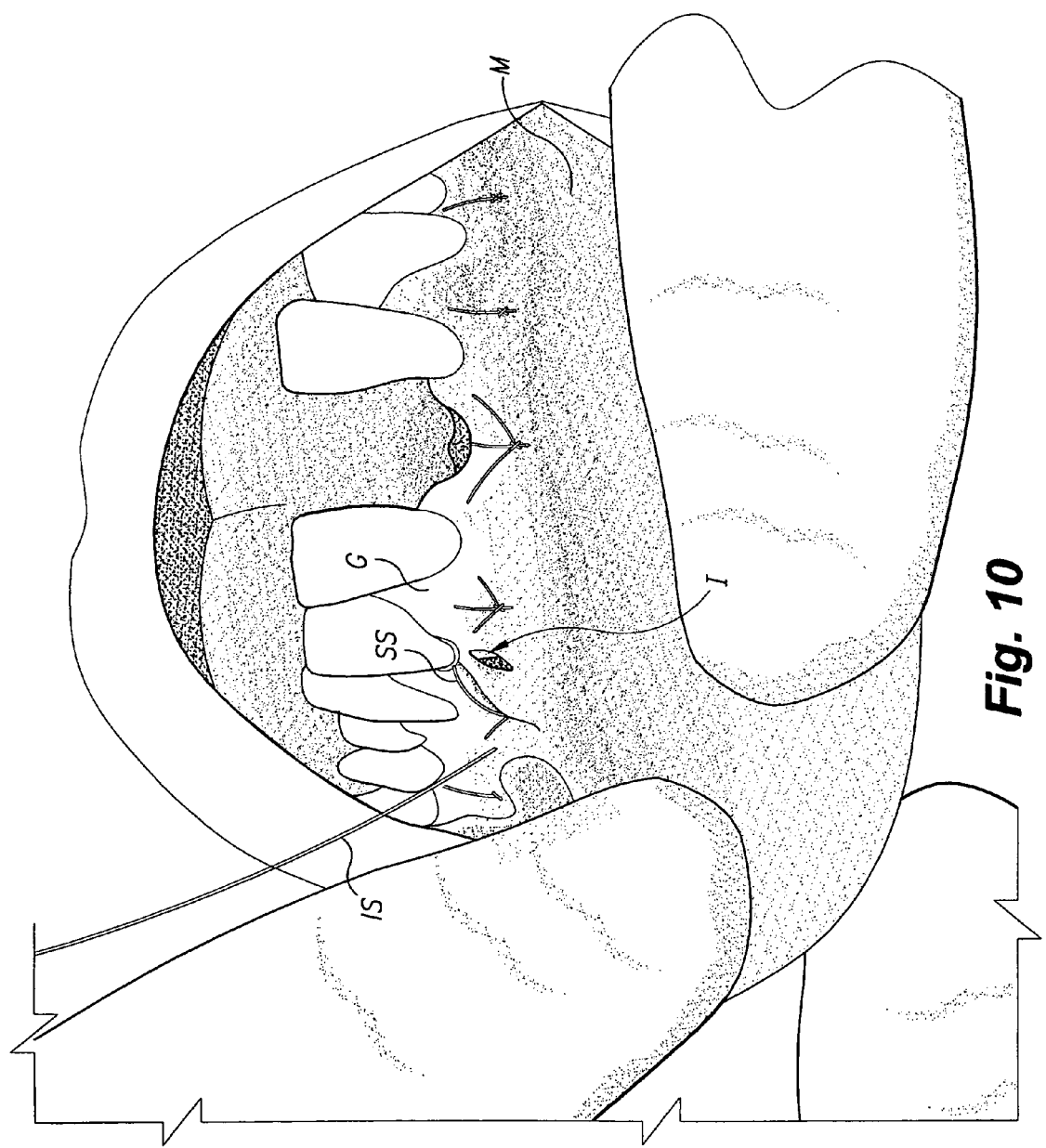
FIG. 10 is a partial perspective view showing the step of closing the pair of vertical incisions in the tunneling method for dental block grafting according to the present invention.
Figure 11:
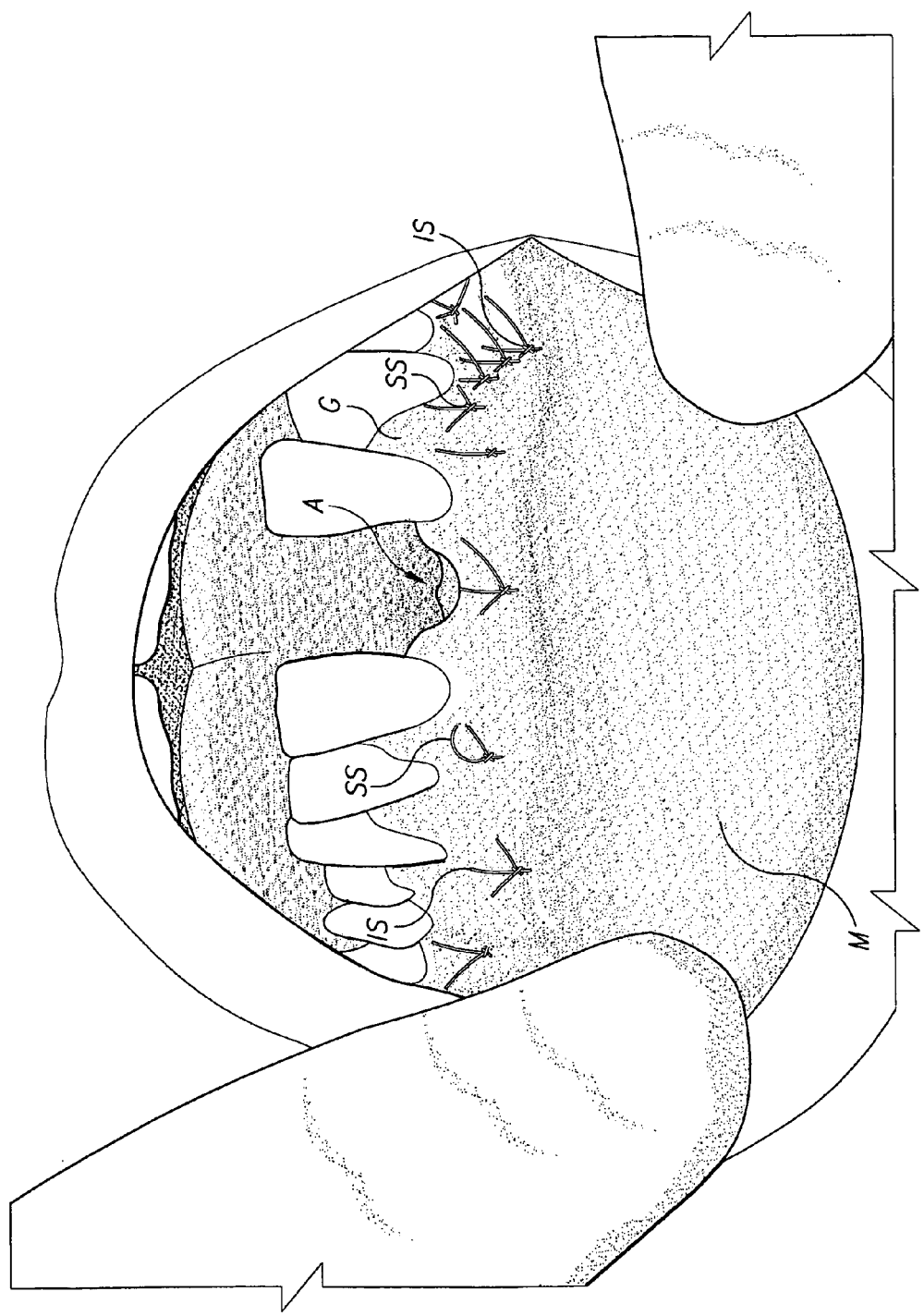
FIG. 11 is a partial perspective view showing the mouth of the patient immediately following suturing in matrix and the vertical incisions in the tunneling method for dental block grafting according to the present invention.
Figure 12:
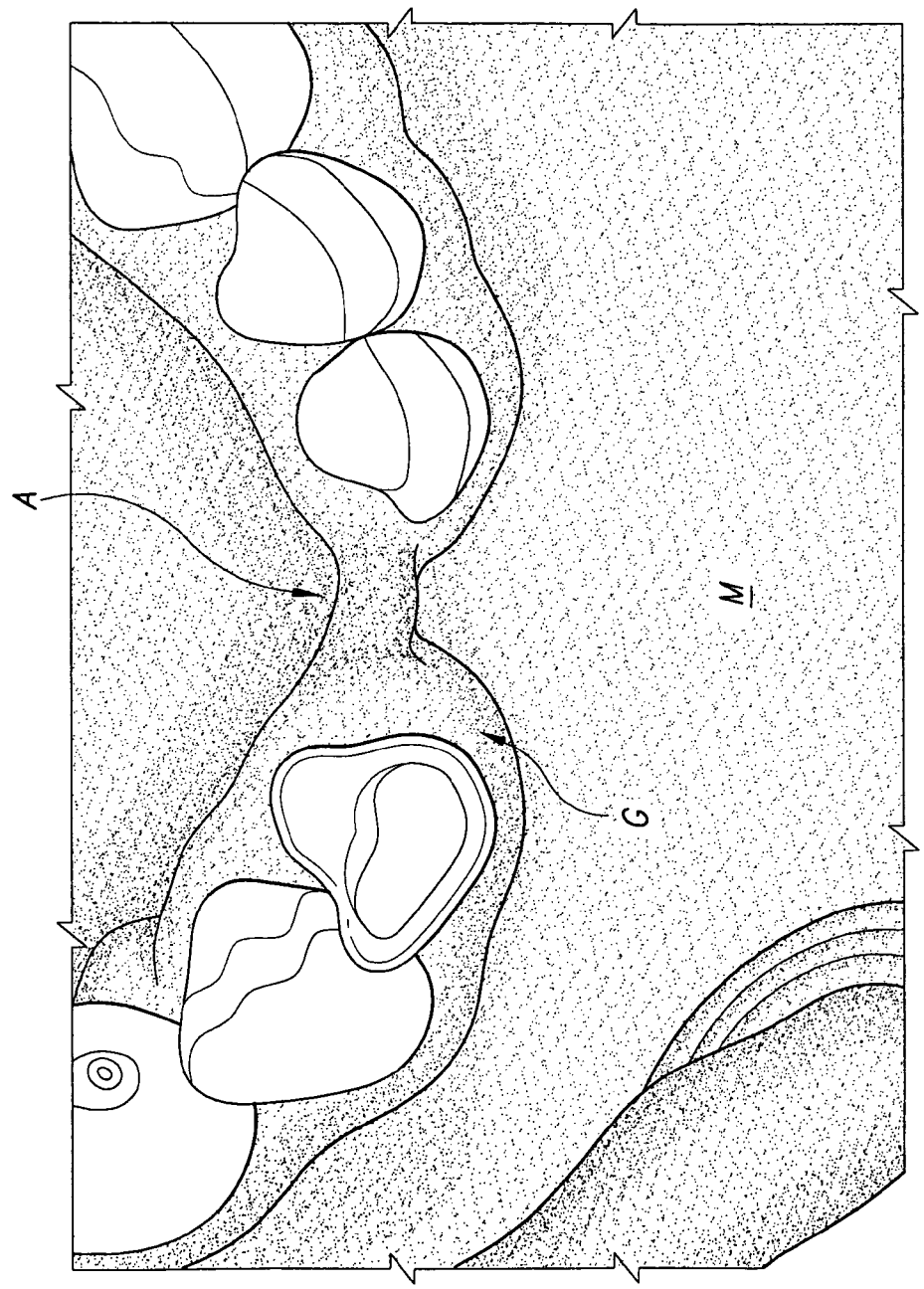
FIG. 12 is a partial perspective view showing the soft tissue of the patient's mouth after implanting the dental matrix and allowing a healing time of approximately eight weeks in the tunneling method for dental block grafting according to the present invention.
Figure 13:
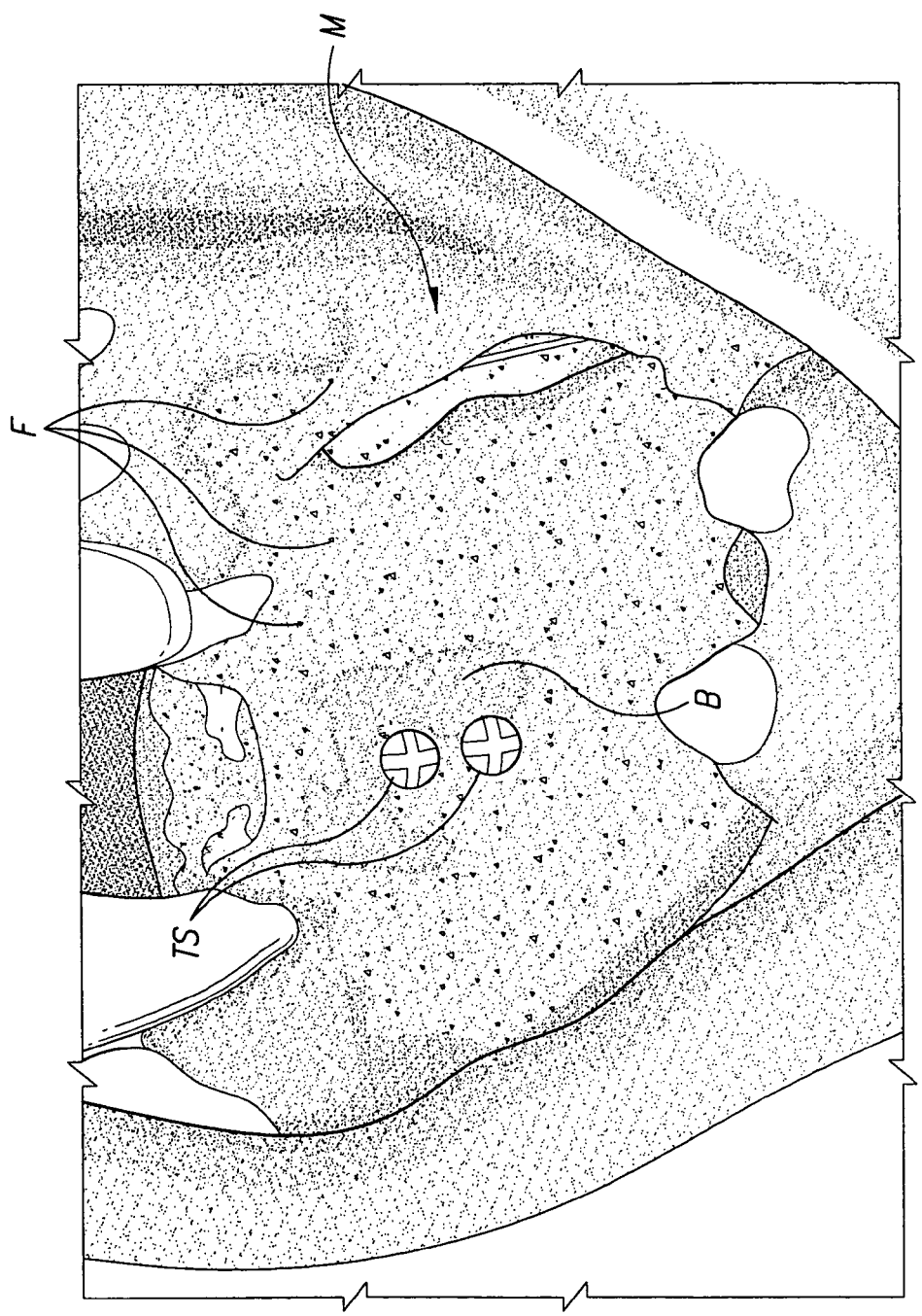
FIG. 13 is a partial perspective view showing the step of fixing of a block graft in the tunneling method for dental block grafting according to the present invention.
Figure 14:
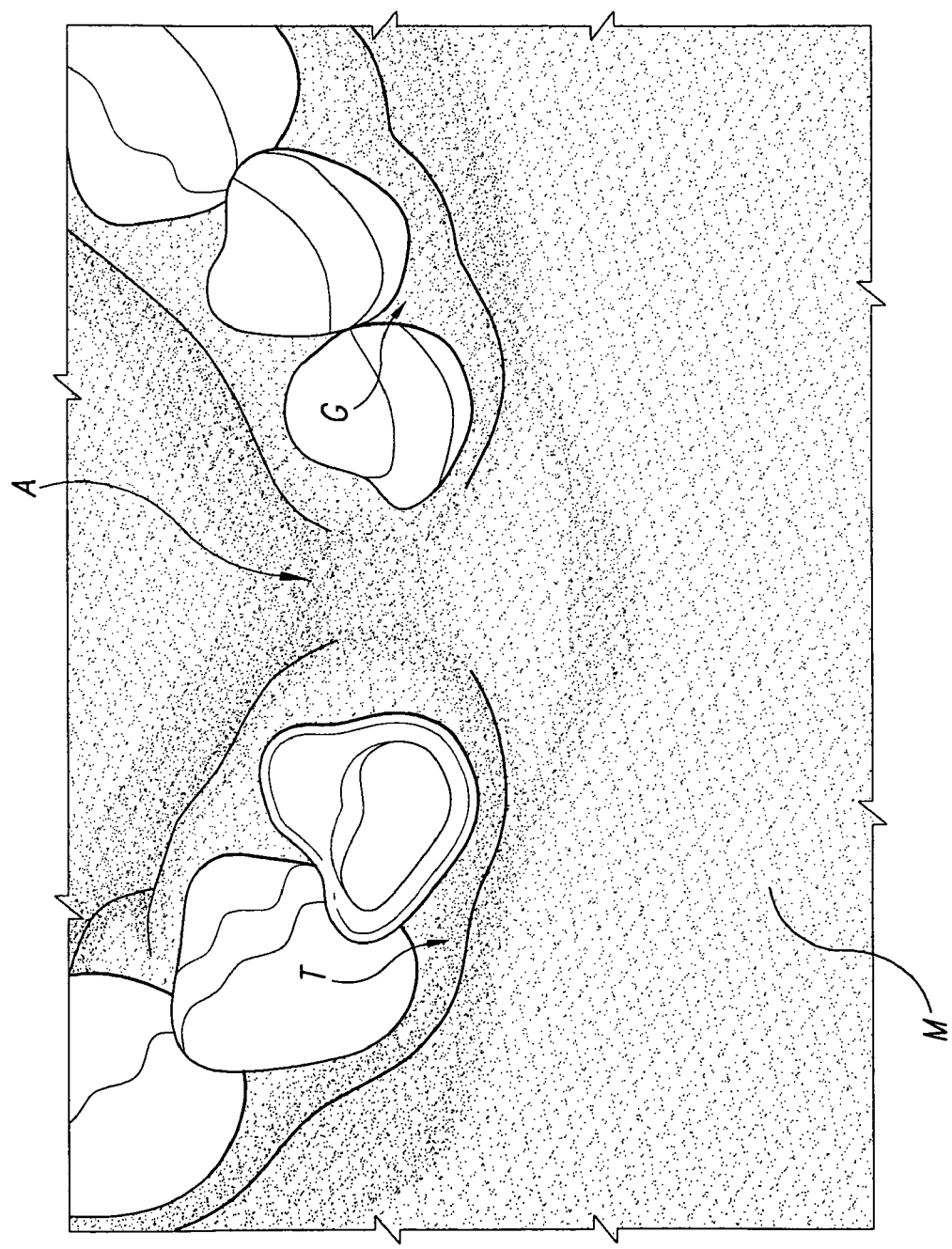
FIG. 14 is a partial perspective view showing the patient's healed mouth after a period of approximately six months following the block graft procedure in the tunneling method for dental block grafting according to the present invention.

As shown in FIG. 10, the pair of incisions I are then closed with interrupted sutures IS (step 24). Preferably, the patient is allowed a healing time of approximately eight weeks between the closing of the incisions I and the fixing of block graft B. FIG. 12 illustrates the healed soft tissue of the patient's mouth after eight weeks. The block graft B is then fixed to the recipient site by pair of titanium screws TS or the like, as shown in FIG. 13 (step 26). Deficiencies at the edges of the graft may be then filled with particulate bone graft F. FIG. 14 illustrates the healed mouth approximately six months following the above surgical procedure with no soft tissue dehiscence or fenestration.

The block grafting surgery is performed as follows: a crestal incision may be made from the mesial of mandibular left central incisor to the mesial of mandibular right lateral incisor, with divergent releasing incisions remote to the defect being used to facilitate closure and maintain adequate blood supply. The recipient site may then be recontoured to improve bone-to-graft contact. The underlying bone is perforated with a small round bur. For the donor site, the mucoperiosteal flap may be reflected toward the inferior border of the mandible. The size and shape of the graft required is marked out with a fissure bur in a surgical handpiece under copious saline irrigation. The superior horizontal osteotomy is then made with a minimal distance of 5 mm from the apices of mandibular incisors and canines. Inferior horizontal osteotomy is made parallel to the inferior border of the mandible. The graft is then elevated from the symphysis with bone chisels, and the donor site is filled with a mixture of bovine bone and calcium sulfate, preferably having a ratio of approximately 4:1.

The graft is then refined to fit into the defect. All sharp edges are rounded, and the graft is fixed to the recipient site using two 1.2 mm diameter titanium screws, as described above. A collagen bioabsorbable membrane may then be used to cover the graft. The periosteum at the base of the flap is then incised to allow stretching of the mucosa M and tension-free adaptation of the wound margins. The flap is then secured using non-resorbable expanded polytetraflouroethylene interrupted sutures or the like.

It is to be understood that the present invention is not limited to the embodiment described above, but encompasses any and all embodiments within the scope of the following claims.

I claim:

1. A tunneling method for dental block grafting, comprising the steps of:
    cutting a pair of incisions in the mucosa of a patient's mouth, each said incision being cut approximately equidistant from a recipient site for a dental implant;
    forming a tunnel in the mucosa extending between, and connecting, said pair of incisions using a dental implement, the dental implement extending through the tunnel;
    extending the tunnel coronally to undermine tissue covering the recipient site;
    suturing an acellular dermal matrix to an exposed end of the dental implement;
    pulling the dental implement through the tunnel to position the acellular dermal matrix within the tunnel;
    positioning the acellular dermal matrix throughout the recipient site;
    fixing the acellular dermal matrix by suturing;
    closing the pair of incisions; and
    fixing a block graft to the recipient site with at least one screw.

2. The tunneling method for dental block grafting as recited in claim 1, wherein each of said incisions is formed a distance of at least one-and-a-half tooth widths from the recipient site.

3. The tunneling method for dental block grafting as recited in claim 2, wherein each said incision extends substantially apically from the mucogingival junction.

4. The tunneling method for dental block grafting as recited in claim 3, wherein each said incision is formed with a length between approximately 5 and 7 mm.

5. The tunneling method for dental block grafting as recited in claim 4, wherein the tunnel is formed by partial-thickness dissection of the mucosa.

6. The tunneling method for dental block grafting as recited in claim 5, wherein the acellular dermal matrix is sutured to the exposed end of the dental implement by a single knot.

7. The tunneling method for dental block grafting as recited in claim 6, wherein the acellular dermal matrix is positioned throughout the recipient site with a periosteal elevator.

8. The tunneling method for dental block grafting as recited in claim 7, wherein the acellular dermal matrix is fixed with suspension sutures.

9. The tunneling method for dental block grafting as recited in claim 8, wherein the acellular dermal matrix is fixed coronally with approximately five suspension sutures.

10. The tunneling method for dental block grafting as recited in claim 9, wherein the pair of incisions are closed by interrupted sutures.

11. The tunneling method for dental block grafting as recited in claim 10, wherein the block grafting is fixed to the recipient site with a pair of screws following a period of healing time from the closing of the incisions.

12. The tunneling method for dental block grafting as recited in claim 11, wherein the period of healing time is approximately eight weeks.

13. The tunneling method for dental block grafting as recited in claim 12, further comprising the step of filling deficiencies at edges of the block graft.

14. The tunneling method for dental block grafting as recited in claim 13, wherein the deficiencies are filled with a mixture of bovine bone and calcium sulfate.

* * * * *